US009541560B2

(12) United States Patent
Denson et al.

(10) Patent No.: US 9,541,560 B2
(45) Date of Patent: Jan. 10, 2017

(54) SEROLOGICAL MARKERS OF INFLAMMATORY BOWEL DISEASE PHENOTYPE AND DISEASE PROGRESSION (71) Applicant: Children's Hospital Medical Center, Cincinnati, OH (US)

(72) Inventors: Lee Denson, Wyoming, OH (US); Bruce Colston Trapnel, Hamilton, OH (US); Kanji Uchida, Tokyo (JP)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 14/686,628

(22) Filed: Apr. 14, 2015

(65) Prior Publication Data
US 2015/0293113 A1 Oct. 15, 2015

Related U.S. Application Data (60) Continuation of application No. 13/114,078, filed on May 24, 2011, now abandoned, which is a division of application No. 12/058,230, filed on Mar. 28, 2008, now abandoned.

(60) Provisional application No. 60/909,153, filed on Mar. 30, 2007.

(51) Int. Cl.
*G01N 33/543* (2006.01)
*G01N 33/68* (2006.01)
*A61K 38/19* (2006.01)
*C07K 16/24* (2006.01)

(52) U.S. Cl.
CPC .......... *G01N 33/686* (2013.01); *A61K 38/193* (2013.01); *C07K 16/241* (2013.01); *G01N 33/68* (2013.01); *G01N 33/6863* (2013.01); *C07K 2317/21* (2013.01); *C07K 2317/24* (2013.01); *C07K 2317/76* (2013.01); *G01N 2333/535* (2013.01); *G01N 2800/065* (2013.01); *G01N 2800/50* (2013.01)

(58) Field of Classification Search
CPC G01N 33/686; G01N 33/6863; G01N 33/543; G01N 33/68; G01N 2333/535; G01N 2800/065; G01N 2800/50; A61K 38/193; C07K 16/241; C07K 2317/21; C07K 2317/24; C07K 2317/76
See application file for complete search history.

(56) References Cited

U.S. PATENT DOCUMENTS 5,932,429 A 8/1999 Targan et al.
6,090,382 A 7/2000 Salfeld et al.
6,183,951 B1 2/2001 Plevy et al.
6,218,129 B1 4/2001 Walsh et al.

OTHER PUBLICATIONS

Fogolin et al., Choice of the adequate quantification method for recombinant human GM-CSF produced in different host systems, Electroneic Journal of Biotechnology, vol. 5, No. 3, Issue of Dec. 15, 2002, pp. 273-250.*
Arnott, I.D.R. et al., "Sero-Reactivity to Microbial Components in Crohn's Disease is I Associated with Disease Severity and Progression, but not NOD2/CARD15 Genotype," Am. J. of Gastroenterol. vol. 99 (2004) pp. 2376-2384.
Amre, D.K. et al., "Utility of Serological Markers in Predicting the Early Occurrence of Complications and Surgery in Pediatric Crohn's Disease Patients," Am. J. Gastroenterol. vol. 101 (2006) pp. 645-652.
Austin, Gregory L. et al., "Positive and Negative Predictive Values: Use of Inflammatory Bowel Disease Serological Markers," Am J. Gastroenterol., vol. 101 (2006) pp. 413-416.
Biagioni, C. et al., "Redox State and $O_2$—Production in Neutrophils of Crohn's Disease Patients," Society for Experimental Biology and Medicine (2006) pp. 186-195.
Bruczynski, M.E., et al., "Molecular Classification of Crohn's Disease and Ulcerative Colitis Patients Using Transcriptional Profiles in Peripheral Blood Mononuclear Cells," J. of Mole. Diagnostics, vol. 8(1) (Feb. 2006) pp. 51-61.
Dubinsky, M.C. et al., "Immunogenetic phenotypes in inflammatory bowel disease,"World J. Gastroenterol., vol. 12(23) (Jun. 21, 2006) pp. 3645-3650.
Dubinsky, M.C. et al., "Serum Immune Responses Predict Rapid Disease Progression among Children with Crohn's Disease: Immune Responses Predict Disease Progression," Am J. Gastroenterol., vol. 101 (2006) pp. 360-367.
Fiorucci, S. et al., "Critical Role of Toll-Like Receptors in Modulating GM-CSF Activity in Rodent Models of Colitis," Gastroenterology, vol. 130 (2006) p. A-108s.
Gupta, S.K., et al., "Comparison of Serological Markers of Inflammatory Bowel Disease with Clinical Diagnosis in Children," Inflamm Bowel Dis, vol. 10(3) (May 2004) pp. 240-244.
Hanauer, S. B., "Inflammatory Bowel Disease: Epidemiology, Pathogenesis, and Therapeutic Opportunities," Inflamm Bowel Dis, vol. 12(1) (Jan. 2006) pp. S3-S9.
Hanna, E. et al., "GM-CSF Efficacy in Murine DSS Colitis is Medicated by Changes in the Function of Plasmacytoid Dendritic Cells," Gastroenterology, vol. 130 (2006) p. A108.
Harbord, M.W.N., et al., "Impaired neutrophil chemotaxis in Crohn's disease relates to reduced production of chemokines and can be augmented by granulocyte-colony stimulating factor," Ailment Pharmacol Ther, vol. 24 (2006) pp. 651-660.
Joossens, S. et al, "The Value of Serologic Markets in Indeterminate Colitis: A Prospective Follow-up Study," Gastroenterology, vol. 122 (2002) pp. 1242-1247.

(Continued)

*Primary Examiner* — Gary W Counts
(74) *Attorney, Agent, or Firm* — Knobbe, Martens, Olson & Bear LLP (57) ABSTRACT

Disclosed are novel biomarkers and methods related to diagnostic tests for the detection and characterization of inflammatory bowel diseases, such as Crohn's disease and ulcerative colitis. In particular, the instant invention relates to novel biomarkers and methods of using such biomarkers to predict disease behavior and severity, to differentiate among disease types, and to optimize selection of treatment options in individuals suspected of having an inflammatory bowel disease.

17 Claims, 3 Drawing Sheets

(56) References Cited

OTHER PUBLICATIONS

Kobayashi, K.S., et al, "Nod2-Dependent Regulation of Innate and Adaptive Immunity in the Intestinal Tract," Science, vol. 307 (Feb. 4, 2005) pp. 731-734.
Krinner, E.M. et al., "A human monoclonal IgG1 potently neutralizing the pro-inflammatory cytokine GM-CSF," Molecular Immunology, vol. 44 (2007) pp. 916-925.
Korzenik, J.R. et al., "Sargramostim for Active Crohn's Disease," N Eng J Med, vol. 352(21) (May 26, 2005) pp. 2193-2201.
Korzenik, J.R. et al., "Is Crohn's Disease an Immunodeficiency? A Hypothesis Suggesting Possible Early Events in the Pathogenesis of Crohn's Disease," Digestive Diseases and Sciences, vol. 45(6) (Jun. 2000) pp. 1121-1129.
Marks, D.J. et al. "Defective acute inflammation in Crohn's disease: a clinical investigation," Lancet, vol. 367 (2006) pp. 668-678.
Lodes, M. J. et al., "Bacterial flagellin is a dominant antigen in Crohn disease," J Clin. Invest., vol. 113 (2004) pp. 1296-1306.
Mow, W.S. et al., "Association of Antibody Responses to Microbial Antigens and Complications of Small Bowel Crohn's Disease," Gastroenterology, vol. 126 (2004) pp. 414-424.
Mow, W.S. et al., "High-Level Serum Antibodies to Bacterial Antigens are Associated with Antibiotic-Induced Clinical Remission in Crohn's Disease: A Pilot Study," Digestive Diseases and Sciences, vol. 49(7/8) (Aug. 2004) pp. 1280-1286.
Sands, B.E., et al., "Design Issues and Outcomes in IBD Clinical Trials," Inflamm Bowel Dis, vol. 11(1) (Nov. 2005) pp. S22-S28.
Satsangi, J., et al., "The Montreal classification of inflammatory bowel disease: controversies, consensus, and implications," gut. bmj.com (Aug. 6, 2008) pp. 749-753.
Self, C.H., et al., "Advances in immunoassay technology," Current Opinion in Biotechnology, vol. 7 (1996) pp. 60-65.
Shibata, Y., et al., "GM-CSF Regulates Alveolar Macrophage Differentiation and Innate Immunity in the Lung through PU.1," Immunity, vol. 15 (Oct. 2001) pp. 557-567.
Teml, A. et al., "Anti-*Saccharomyces cerevisiae* Antibodies: A Stable Marker for Crohn's Disease During Steroid and 5-Aminosalicylic Acid Treatment," Am. J. Gastroenterol, vol. 98(100) (203) pp. 2226-2231, 2003.
Tomer, G. et al., "NOD2/CARD15 Variants are Associated with Lower Weight at Diagnosis in Children with Crohn's Disease," Am. J. Gastroenterol. vol. 98(11) (2003) pp. 2479-2484.
Trapnel, B.C. et al., "Pulmonary Alveolar Proteinosis," N Eng J Med, vol. 349(26) (Dec. 25, 2003) pp. 2527-2539.
Uchida, K. et al., "GM-CSF Autoantibodies and Neutrophil Dysfunction in Pulmonary Alveolar Proteinosis," N Eng J Med, vol. 356(6) (Feb. 8, 2007) pp. 567-579.
Uchida, K. et al., "High-affinity autoantibodies specifically eliminate granulocyte-macrophage colony-stimulating factor activity in the lungs of patients with idiopathic pulmonary alveolar proteinosis," Blood, vol. 103(3) (Feb. 1, 2004) pp. 1089-1098.
Vind, I. et al., "Increasing Incidences of Inflammatory Bowel Disease and Decreasing Surgery Rates in Copenhagen City and County, 2003-2005: A Population -Based Study from the Danish Crohn Colitis Database," Am J. Gastroenterol, vol. 101 (2006) pp. 1274-1282.
Walker, L.J. et al., "Anti-*Saccharomyces cerevisiae* antibodies (ASCA) in Crohn's disease are associated with disease severity but not NOD2/CARD15 mutations," Clin Exp. Immunol, vol. 135 (2004) pp. 490-496.
Wittmann, S. et al., "Cytokine Upregulation of Surface Antigens Correlates to the Priming of the Neutrophil Oxidative Burst Response," Cytometry Part A 57A (2004) pp. 53-62.
Zholudev, A., et al. "Serologic Testing with ANCA, ASCA and Anti-OmpC in Children and Young Adults with Crohn's Disease and Ulcerative Colitis: Diagnostic Value and Correlation with Disease Phenotype," Am J. Gastroenterol. vol. 99 (2004) pp. 2235-2241.
Louis, et al.; "Early Development of Stricturing or Penetrating Pattern in Crohn's Disease is influenced by Disease Location, Number of Flares, and Smoking but not by NOD2/CARD15 Genotype," Gut, 52(4), pp. 552-557, Apr. 2003.

\* cited by examiner

SEQUENCE LISTING

```
<160> NUMBER OF SEQ ID NOS: 1

<210> SEQ ID NO 1
<211> LENGTH: 127
<212> TYPE: PRT
<213> ORGANISM: Homo sapiens

<400> SEQUENCE: 1

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
            115                 120                 125
```

SEROLOGICAL MARKERS OF INFLAMMATORY BOWEL DISEASE PHENOTYPE AND DISEASE PROGRESSION

CROSS-REFERENCE TO RELATED APPLICATIONS

This application claims priority to U.S. Provisional Patent Application Ser. No. 60/909,153, which was filed on Mar. 30, 2007, the entirety of which is incorporated herein by reference for all purposes.

This invention was made with government support under DK068164 awarded by the National Institutes of Health. The government has certain rights in the invention.

BACKGROUND OF THE INVENTION

The incidence of the Inflammatory Bowel Diseases (IBD), Crohn's Disease (CD) and Ulcerative Colitis (UC) has increased dramatically over the past four decades with approximately five million individuals affected in North America and Europe. While therapeutic options have increased over the past decade, the ability to classify subtypes of IBDs, predict disease progression and behavior, and target newer biologic therapies to specific subgroups of patients has lagged behind. This has led to an empiric step-up approach to therapy, in which increasingly more potent agents are offered until an effective regimen is identified.

The inflammatory bowel diseases are believed to be caused by a complex interaction between genetic susceptibility and environmental triggers leading to chronic relapsing intestinal inflammation (Bouma, G. 2003). CD is characterized by discontinuous transmural inflammation which can involve any part of the gastrointestinal (GI) tract, although the terminal ileum and proximal colon are most commonly involved (Hanauer S. B. 2006). Conversely, UC is characterized by continuous superficial inflammation limited to the colon, beginning in the rectum and extending proximally (Hanauer S. B. 2006).

IBDs can be difficult to diagnose, a diagnosis being obtained only after extensive, costly, and often invasive procedures have been performed. An initial diagnosis, made on the basis of medical history and physical examination, is generally confirmed via imaging of the intestines and laboratory culture tests to rule out bacterial, viral and parasitic infections. Colonoscopy may also be used to image the intestines and colon, such that the entire intestines can be evaluated to distinguish between IBDs on the basis of the location of ulcerations (Crohn's disease affects some areas of the intestines and skips over others, while ulcerative colitis is more indiscriminate). Endoscopy may also be used to biopsy the intestinal tissue, which can be used to identify the deep inflammation of the bowel that is characteristic of Crohn's disease. Further, X-rays (after oral or rectal ingestion of Barium), computed tomography (CT) scan, and magnetic resonance imaging (MRI) may be helpful in locating fistulas and assisting in the diagnosis. A stool analysis (including a test for blood in the stool) is often performed, depending on symptoms, to look for blood and signs of bacterial infection. Blood and urine tests may be done to check for anemia, high white cell counts, or malnutrition—all signs of IBDs. Finally, the conditions may go undiagnosed for years as symptoms usually develop gradually and less than all of the intestines may be involved. As such, while there is currently no reliable biochemical test available for IBD or to distinguish subtypes of the disease, such a test would be highly valuable in curtailing cost and the physical discomfort endured by individuals in obtaining an IBD diagnosis.

With current diagnostic approaches, approximately 60% of IBD patients are classified as CD, 30% as UC, and 10% as indeterminate colitis (IC) (Kugathasan S. 2003). Patients with IC have intestinal inflammation limited to the colon, without specific endoscopic or histological features diagnostic of either CD or UC. A diagnosis of IC limits the ability to predict clinical disease behavior and outcome following surgery, and prevents patients with refractory disease from entering into clinical trials of new agents.

IBD causes substantial morbidity including frequent hospitalizations and surgeries, and longstanding disease is complicated by cancer (Hanauer S. B. 2006). It is likely that there are several immunogenetic sub-types of IBD, with CD and UC representing the broadest clinical classifications (Dubinsky M. C. 2006). Current evidence suggests that CD results when mucosal tolerance to the enteric flora is lost (Bouma G. 2003, Lodes M. J. 2004). CARD15/NOD2, an intra-cellular sensor for the bacterial product muramyl dipeptide, is expressed in intestinal epithelial cells (IEC) and macrophages and participates in anti-microbial defenses (Houma G. 2003, Kobayashi K. S. 2005). Loss of function mutations in NOD2 increases susceptibility to CD primarily involving the ileum (Tomer G 2003).

A variety of defects in neutrophil function have also been described in CD (Korzenik J. R. 2000). These primary defects in mucosal innate immunity may then lead to activation of intestinal antigen presenting cells (APG) and expansion of $T_{eff}$ reactive to the host flora (Bouma G. 2003, Lodes M J 2004). The immunogenetic basis for differences in ileal versus colonic involvement in CD is not known, although mounting evidence suggests that defects in innate immunity and loss of tolerance to bacterial antigens are predominately associated with small bowel disease. Mutations in CARD15 are associated with ileal disease and growth failure in children, while seroreactivity to microorganism components (ASCA, OmpC, CBir1, and I2 antibodies) is associated with small bowel, stricturing disease (Tomer G 2003), (Mow W. S. 2004). This does not appear to be the case for UC, in which defects in epithelial repair and xenobiotic detoxification are implicated (Dignass A. U. 2004). The introduction of biologic therapies targeting specific components of the mucosal immune response has improved outcomes for patients with IBD. However, sustained remissions have not been observed in more than fifty percent of individuals with any new biologic agent.

Current Therapies for Inflammatory Bowel Diseases

Current options for induction of remission in IBD include mesalamine, corticosteroids, methotrexate, and infliximab. Options for maintenance of remission include mesalamine, the immunomodulators 6-mercaptopurine/azathioprine (6-MP/AZA), methotrexate, and infliximab. The most common first line regimen includes induction of remission with prednisone, and maintenance of remission with 6-MP/AZA. In the absence of a reliable test to predict response to therapy, patients are empirically offered agents for induction and maintenance of remission largely based upon disease severity and location. As the effectiveness of any one agent is typically on the order of 50% to 80%, this leads to a substantial number of patients receiving a series of ineffective agents, with attendant side effects, before an effective regimen is identified.

Despite the recent advent of the biologic therapies, corticosteroids remain the predominant first line choice for induction of remission in moderate to severe IBD. Typically, 50% of patients will go into remission and then be able to wean corticosteroids within three months. However, 20% will not respond, and 30% will not be able to discontinue steroids; these groups are termed steroid refractory (SR) and steroid dependent (SD), respectively.

Inflammatory Bowel Disease Markers for Diagnosis and Progression of Disease

In recent years, serological markers which largely comprise antibodies reactive to the host flora have been extensively studied in an attempt to improve IBD classification and prediction of disease progression. However, these markers have not proven effective in definitively characterizing IBD patients as CD or UC, and have not been able to predict with sufficient accuracy which patients are most likely to require surgery for the condition.

The first serological markers to be described in IBD were the anti-*saccharomyces cervisiae* antibody (ASCA) and anti-neutrophil cytoplasmic antibody with perinuclear staining (pANCA) (Austin G. L. 2006). Subsequently, additional markers including antibodies to the outer membrane porin protein C (OmpC) of *E. Coli*, to *Pseudomonas fluorescens* (I2) and to flagellin (CBir1) have been described (Dubinsky M. C. 2006). Whether any of these antibodies are pathogenic is not known, although recent evidence points to bacterial flagellin as a critical antigen in CD (Lodes M. J. 2004). pANCA has been associated with UC, while the other markers have been associated with CD. A recent series of well-characterized adult CD patients demonstrated a frequency of 37% for OmpC, 52% for I2, 39% for ASCA, and 14% for pANCA (Arnott I. D. 2004). The frequency of pANCA in UC is typically 60% to 70% (Austin G. L. 2006). Multiple studies have been performed to determine whether levels of these antibodies can be used to screen for IBD in patients with suggestive symptoms, and to discriminate CD from UC, thereby reducing the number of cases of IC. However, the sensitivity of pANCA for UC in recent adult and pediatric series has ranged from 63% to 70%, while the sensitivity of ASCA for CD ranged from 44% to 72% (Linskens R. K. 2002), (Zholudev A. 2004), (Gupta S. K. 2004). Thus, these results demonstrate that these markers are not sufficiently sensitive to be used as effective screening tools. In terms of specificity, these assays perform substantially better, and range from 86% to 95% for pANCA for UC and from 82% to 95% for ASCA for CD (Linskens R. K. 2002, Zholudev A. 2004, Gupta S. K. 2004). From 10% to 18% of CD patients will be positive for pANCA, these typically have Crohn's colitis (Zholudev A. 2004). In cohorts of patients with a high prevalence of IBD (42% to 68%), this has led to a reported positive predictive value (PPV) of 90% to 96% for both CD and UC, and a negative predictive value (NPV) of 50% to 80% (Austin G. L. 2006, Gupta S. K. 2004). Therefore, as recently reviewed by Austin et al, these tests perform best when used in a patient population with a high pre-test probability of having IBD (Austin G. L. 2006). As such, there is a need for improved markers having improved sensitivity and selectivity that can be used as effective screening tools to diagnose and differentiate inflammatory bowel diseases.

IBD patients further have variable risk of needing surgery to treat the disease. Current standard clinical approaches are not able to further reduce the number of diagnoses of IC, or to predict which patients will be most likely to progress to surgery. From about 30% to 50% of IBD patients will fail medical therapy and progress to surgery within 3 to 10 years of diagnosis (Austin G. L. 2006). Most CD patients initially present with inflammatory disease (80%), and over the next 10 years may progress to stricturing and/or penetrating behavior, categorized as B2/B3-type disease (Hanauer S. B. 2006). Patients with stricturing/penetrating disease then frequently require surgery.

Several groups have performed studies to determine whether IBD serology can predict disease progression and the need for surgery (Mow W. S. 2004). Consistently, high titer ASCA+CD patients have been more likely to have fibrostenosing small bowel disease and require ileocecal resection (36% vs 13% in one recent pediatric series) (Arnott I. D. 2004). Conversely, pANCA+CD patients are more likely to have colonic disease and not require resection. Recent reports demonstrated that the combined magnitude of reactivity to microbial components (ASCA, OmpC, and I2) predicted a phenotype of more severe small bowel CD with progression to surgery in adult patients (Arnott T. D. 2004). However, the magnitude of the serological response did not predict the need for 6-MP or infliximab. Importantly, the association was also independent of the CARD15 genotype, which has also been associated with small bowel CD and progression to surgery (Arnott I. D. 2004, Walker L. K. 2004).

Recent reports in pediatrics have demonstrated very similar predictive characteristics High titer ASCA+CD patients were more likely to require surgery sooner than ASCA-patients (Amre D. K. 2006). In a study measuring ASCA, OmpC, I2, and CBir1 reactivity, the presence and magnitude of response of these was associated with a higher rate of progression to a stricturing or penetrating complication over the first 18 months following diagnosis (Dubinsky M. C. 2006). Potentially this sub-group of CD patients would benefit from earlier institution of targeted biologic therapies more likely to prevent disease progression. In this regard, Mow et al have recently reported a trend towards improved responses to antibiotics in CD patients sero-reactive to OmpC and/or I2, and decreased responses to a steroid preparation, budesonide (Mow W. S. 2004).

A limitation of this approach is the substantial number of patients who experience disease progression and require surgery who are sero-negative for these markers. For example, in the Arnott report, 96 CD patients were negative for ASCA or OmpC/I12, and fifty percent of those experienced disease progression and required surgery (Arnott I. D. 2004). This compared to 40 CD patients who were sero-positive, with rates of disease progression and surgery of 90% and 75%, respectively (Arnott I. D. 2004). Therefore, additional approaches are needed to complement current serological assays in defining clinically important sub-types of IBD with respect to disease behavior and progression.

Current biomarkers have failed to be effectively used to provide diagnostic tests for classifying, characterizing or predicting the outcome of inflammatory bowel diseases. In particular, current biomarkers have not been efficacious in distinguishing among the various subtypes of inflammatory bowel diseases. Accordingly, there is a need for biomarkers that can form the basis for diagnostic tools that can effectively classify, characterize and predict the severity of inflammatory bowel disease.

There is further the need for biomarkers that can be used to predict disease progression, including the likelihood that an individual will require surgery despite treatment with first line therapies would be invaluable. Such markers would allow the clinician to identify the subset of patients at an early stage of disease progression who would benefit from earlier introduction of second or third line therapies, or therapies particularly effective in treatment of a particular subset of IBD, such as anti-TNFα (for example, Remicade or Humira) and/or GM-CSF (Leukine) or the like. The instant invention satisfies these needs and provides related advantages as well.

BRIEF SUMMARY OF THE INVENTION

The present invention relates to biological markers and methods of using biological markers for the diagnosis and prognosis of inflammatory bowel diseases.

The present invention further relates to biological markers that may be used to predict and characterize disease behavior in individuals having an inflammatory bowel disease.

The present invention further relates to biological markers that may be used to predict disease progression, such as the likelihood that an individual having an inflammatory bowel disease, particularly Crohn's disease, will require surgery.

The present invention further relates to a method of classifying an individual with a particular subtype of inflammatory bowel disease, comprising the steps of obtaining a biological sample from an individual suspected of having an inflammatory bowel disease; determining the concentration of anti-GM-CSF antibodies in the sample; and correlating the concentration of anti-GM-CSF antibodies in the sample to known standards.

In yet another aspect, the instant invention provides a method of diagnosing an individual with a particular subtype of inflammatory bowel disease, comprising the steps of obtaining a biological sample from an individual suspected of having an inflammatory bowel disease, determining the concentration of anti-GM-CSF relative to neutrophil function, IBD phenotype, CARD15 variants or commercial inflammatory bowel disease serology; correlating the results to known standards; and diagnosing the individual based on these results.

In yet a further aspect, the present invention relates to a method for predicting the severity of an inflammatory bowel disease in an individual, particularly whether the individual will require surgery, comprising the steps of obtaining a biological sample from the individual suspected of having or having an inflammatory bowel disease; determining the concentration of anti-GM-CSF antibodies in the sample; and correlating the concentration of anti-GM-CSF antibodies in the sample to known standards to predict the severity of the inflammatory bowel disease, particularly whether an individual will require surgery In this aspect of the invention, the method may be used to identify the appropriate therapy for an individual based on the determination of elevated anti-GM-CSF antibodies.

In yet another aspect, the present invention relates to a method for predicting the appropriate therapeutic treatment for an inflammatory bowel disease, comprising the steps of obtaining a biological sample from an individual suspected of having an inflammatory bowel disease; determining the concentration of anti-GM-CSF antibodies in the sample; and correlating the concentration of anti-GM-CSF antibodies in the sample to known standards to select the appropriate therapeutic treatment for the inflammatory bowel disease, wherein elevated anti-GM-CSF antibodies indicate that the patient is a candidate for therapies selected from anti-TNFα therapy, GM-CSF administration, or combinations thereof.

In another aspect of the present invention, determination of GM-CSF dependent up-regulation of cell surface CD11b may be used as a diagnostic assay to distinguish between UC and CD patients.

The present invention further relates to kits embodying the above described methods, such as a kit for determining a diagnosis or a prognosis of an individual suspected of having or having an inflammatory bowel disease, which comprises at least a probe specific for GM-CSF wherein the probe is capable of detecting a concentration of anti-GM-CSF antibodies, such that a diagnosis or prognosis of the individual may be made.

The present invention further relates to immunoassays for the qualitative or quantitative determination, in a sample from an individual, of anti-GM-CSF antibodies wherein the immunoassay comprises the steps of obtaining a sample from an individual suspected of having or having an inflammatory bowel disease, providing an immobilized antigen reactive to anti-GM-CSF antibodies, contacting the sample with the antigen to form an antigen-antibody complex, washing the complex to remove non-specifically bound components, followed by detecting the captured anti-GM-CSF antibodies.

DETAILED DESCRIPTION OF THE INVENTION

Current care and clinical trials for patients with IBD is hampered by a lack of biomarkers to predict and monitor response to therapy or progression of disease. Without biomarkers that allow prediction of a patient's responsiveness to current therapies, patients are offered therapies via an empiric approach with results in, at best, a 50% rate of sustained remission, while subjecting many patients to unnecessary side effects and expense, further delaying recovery and improved quality of life. As such, identification of biomarkers offers the opportunity to define distinct immunogenetic sub-types of disease which may benefit from specific treatment approaches.

For example, the availability of sensitive biomarker would permit the treating physician to evaluate a patient's likely responsiveness to first line or second line therapeutics. The prediction of the patient's likely response permits the physician to select therapies likely to be most efficacious for a given individual, avoiding treatment with less useful therapies. This, in turn, avoids subjecting the patient to unnecessary side effects and expense, while improving the patient's quality of life and creating opportunities to delay or prevent disease progression.

Definitions

Unless defined otherwise, technical and scientific terms used herein have the same meaning as commonly understood by one of ordinary skill in the art to which this invention belongs Singleton et al., Dictionary of Microbiology and Molecular Biology 2nd ed., J. Wiley & Sons (New York, N.Y. 1994), provide one skilled in the art with a general guide to many of the terms used in the present application.

For purposes of the present invention, the following terms are defined below.

The articles "a" and "an" are used herein to refer to one or to more than one (i.e., to at least one) of the grammatical object of the article. By way of example, "an element" means one element or more than one element.

A "biological sample" encompasses any sample obtained from a living system or subject. The definition encompasses blood, serum, tissue, and other samples of biological origin that can be collected from a living system, subject or individual In one embodiment, biological samples are obtained through sampling by minimally invasive or non-invasive approaches (e.g., urine collection, stool collection, blood drawing, needle aspiration, and other procedures involving minimal risk, discomfort or effort). Biological samples can be gaseous (e.g., exhaled breath). Biological samples are often liquid (sometimes referred to as a "biological fluid"). Liquid biological samples include, but are not limited to, urine, blood, interstitial fluid, edema fluid, saliva, lacrimal fluid, inflammatory exudates, synovial fluid, abscess, empyema or other infected fluid, cerebrospinal fluid, sweat, pulmonary secretions (sputum), seminal fluid, feces, bile, intestinal secretions, and others. Biological samples include samples that have been manipulated in any way after their procurement, such as by treatment with reagents, solubilization, or enrichment for certain components, such as proteins or polynucleotides. The term "biological sample" also encompasses a clinical sample such as serum, plasma, other biological fluid, or tissue samples, and also includes cells in culture, cell supernatants and cell lysates.

As used herein, the term "biomarker" refers to a physical, biochemical, or physiologic measurement from or on the organism that represents a true or intended mechanistic target of a compound or a mechanistic event believed to be responsible for, or contributing in, a causal manner to the initiation, progression, severity, pathology, aggressiveness, grade, activity, disability, mortality, morbidity, disease subclassification or other underlying pathogenic or pathologic feature of one or more diseases. A biomarker may be the target for monitoring the outcome of a therapeutic intervention (i.e., the functional or structural target of a drug agent). "Biomarker" refers to biochemical processes that are involved in, or are believed to be involved in, the etiology or progression of a disease or disorder. The biochemical process (i.e., the flow of molecules through a targeted metabolic pathway or network) is the focus of analysis (as disclosed herein) since it is the underlying changes of the biochemical process (i.e., molecular flux rates) that may be the significant or authentic target for treatment or diagnostic monitoring of the disease or disorder.

The terms "drug," "pharmaceutically active agent," "bioactive agent," "therapeutic agent," and "active agent" may be used interchangeably and refer to a substance, such as a chemical compound or complex, that has a measurable beneficial physiological effect on the body, such as a therapeutic effect in treatment of a disease or disorder, when administered in an effective amount. Further, when these terms are used, or when a particular active agent is specifically identified by name or category, it is understood that such recitation is intended to include the active agent per se, as well as pharmaceutically acceptable, pharmacologically active derivatives thereof, or compounds significantly related thereto, including without limitation, salts, pharmaceutically acceptable salts, N-oxides, prodrugs, active metabolites, isomers, fragments, analogs, solvates hydrates, radioisotopes, etc.

The phrase "effective amount" refers to that amount of a substance that produces some desired local or systemic effect at a reasonable benefit/risk ratio applicable to any treatment. The effective amount of such substance will vary depending upon the individual and disease condition being treated, the weight and age of the individual, the severity of the disease condition, the manner of administration and the like, which can readily be determined by one of ordinary skill in the art.

An "individual" is a vertebrate, preferably a mammal, more preferably a human.

The term "prophylactic" or "therapeutic" treatment is art-recognized and refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The phrase "therapeutic effect" is art-recognized and refers to a local or systemic effect in animals, particularly mammals, and more particularly humans caused by a pharmacologically active substance The term thus means any substance intended for use in the diagnosis, cure, mitigation, treatment or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the individual and disease condition being treated, the weight and age of the individual, the severity of the disease condition, the manner of administration and the like, which can readily be determined by one of ordinary skill in the art.

The term "treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

The practice of the present invention will employ, unless otherwise indicated, conventional techniques of molecular biology (including recombinant techniques), microbiology, cell biology and biochemistry, which are within the skill of the art.

All references cited herein are incorporated in their entirety by reference.

The present invention relates to biomarkers that may be used to characterize individuals having an inflammatory bowel disease. In one aspect, the present invention provides novel biomarkers for inflammatory bowel disease that may be used to diagnose subtypes of the disease. In particular, the biomarkers as disclosed herein may be used to characterize inflammatory bowel disease behavior and progression. In yet another aspect, the invention provides novel biomarkers that may be used to predict the likelihood that an individual diagnosed with an inflammatory bowel disease will require surgical intervention.

Further, the biomarkers and methods disclosed herein may be used in the targeted care of individuals having inflammatory bowel disease. In this aspect of the invention, Crohn's disease patients having a high anti-GM-CSF level are identified as high risk for disease progression and surgery, and may be offered second or third line therapies earlier in their treatment. For example, Crohn's disease patients having elevated anti-GM-CSF antibodies would be candidates for earlier treatment with anti-TNFα therapy (Remicade or Humira), GM-CSF therapy (Leukine) or similar therapies.

A variety of defects in neutrophil function have been described in CD, without a clear etiology (Korzenik J. R. 2000). These have included reduced phagocytosis, adhesion, chemotaxis, and oxidative burst Functionally, this has been shown to paradoxically reduce neutrophil accumulation at sites of acute ileal or rectal injury (Harbord M. W. 2006, Mow W. S. 2004). This may in turn promote accumulation of bacterial products and stimulation of the mucosal adaptive immune system Granulocyte-macrophage colony-stimulating factor (GM-CSF) is a protein secreted by macrophages that functions as a white blood cell growth factor. GM-CSF and its Role in the Regulation of Myeloid Cell Functions.

GM-CSF is a 23 kD, homodimeric cytokine expressed present in serum and tissues with pleiotropic regulatory effects on the functions of myeloid cells (neutrophils, monocytes, eosinophils, tissue macrophages and dendritic cells). The biological effects of GM-CSF are mediated by cell-surface receptors, comprised of α (CDw116) and β chains (CD131) and, in macrophages and neutrophils include increased phagocytosis, cell-surface levels of CD11b (an adhesion molecule), CD11b, cell adhesion, bacterial killing, surfactant catabolism (in alveolar macrophages) (Trapnell, B. et al., NEJM, 2003, incorporated herein by reference). GM-CSF also primes phagocytosis, oxidative burst, and bactericidal activity in neutrophils. In vitro stimulation with GM-CSF restores the function of CD neutrophils, and GM-CSF administration reduces mucosal injury in murine colitis due to trinitrobenzenesulfonic acid (TNBS) or dextran sodium sulfate (DSS) administration (Hanna E. 2006), (Fiorucci S. 2006) (Biagioni C. 2006).

While it has been known for some time that GM-CSF could modulate the functions of myeloid cells, a critical role for GM-CSF in myeloid cell function was discovered by the serendipitous observation that mice deficient in GM-CSF due to gene ablation (GM-CSF knockout mice) develop a lung phenotype that is histologically, biochemically, ultrastructurally and physiologically similar to the human disease known as pulmonary alveolar proteinosis (PAP) (Trapnell, NEJM, 2003). PAP in mice is caused by abrogation of the effects of GM-CSF signaling on myeloid cell functions, due to ablation of the genes encoding either GM-CSF or its receptor. Either genetic manipulation results in a reduction in the ability of alveolar macrophages to degrade or catabolize surfactant. (Shibata, et al., Immunity, 2001, incorporated herein by reference.) Abrogation of GM-CSF signaling also increases the risk of infection due to loss of the stimulatory effects of GM-CSF on neutrophils (Uchida, et al, NEJM, 2007). The stimulatory effects of GM-CSF on macrophages and neutrophils are known as 'priming', and are known to augment the antimicrobial functions of these cells, and thus, also augments innate immune host defenses.

GM-CSF Autoantibodies and their Role in Myeloid Cell Functions.

Human primary PAP is a rare disorder in which surfactant within pulmonary alveoli accumulates, thereby causing respiratory insufficiency (Trapnell et al, NEJM, 2007). Primary PAP is specifically associated with high levels of autoantibodies against granulocyte/macrophage-colony stimulating factor (GM-CSF) that neutralize the biological activity of GM-CSF and are present in vast excess of GM-CSF in vivo. Based on studies in mice, it is believed that pulmonary GM-CSF stimulates the terminal differentiation of alveolar macrophages including many of the effects of GM-CSF on alveolar macrophages. A recent study has now established that GMCSF autoantibodies abrogate the effects of GM-CSF on neutrophils in patients with primary PAP (Uchida et al, NEJM, 2007, incorporated herein by reference). Loss of the effects of GM-CSF on neutrophil function caused by GM-CSF autoantibodies provides a mechanistic explanation for the morbidity and mortality from infection in patients with primary PAP.

The molecular basis for the defects in neutrophil function which have been described in CD, but not UC, is not known. However, GM-CSF and GM-CSF receptor levels are typically elevated in patients with active CD, suggesting the role of a serum inhibitory factor. Recent reports demonstrating that GM-CSF can correct CD neutrophil function in vitro, and that GM-CSF administration can relieve symptoms and reduce intestinal inflammation in a sub-set of CD patients, have also pointed to a potential role for alterations in GM-CSF bioactivity (Biagioni C. 2006, Korzenik J. R. 2005). It has also been determined that very high levels of anti-GM-CSF auto-antibodies impair neutrophil function and cause the rare lung disease, PAP (Uchida K., et al., Blood 2004, incorporated herein by reference). Neutralizing anti-GM-CSF auto-antibodies have been characterized in patients with the rare lung disease Pulmonary Alveolar Proteinosis (PAP). (Uchida K. 2004). Higher levels of anti-GM-CSF inhibit myeloid cell function in patients with the rare lung disease PAP. It has been reported that anti-GM-CSF auto-antibodies suppress systemic innate immunity, by preventing GM-CSF priming of monocyte and neutrophil anti-microbial functions. (Vindi I. 2006). These auto-antibodies have been linked to defects in macrophage and neutrophil function and development of disease (Uchida K. 2004).

GM-CSF is currently undergoing phase II clinical trials in CD, with clinical responses reported in approximately fifty percent of patients (Korzenik J. R. 2005). However, a pro-inflammatory role for GM-CSF has also been invoked for autoimmune diseases including rheumatoid arthritis, and neutralizing anti-GM-CSF antibodies are also in development as potential therapeutic agents (Krinner E. M. 2006). Moreover, most patients with active CD or UC have increased production of GM-CSF in the inflamed intestine, and increased local expression of the GM-CSF receptors. Endogenous anti-GM-CSF antibodies may regulate local GM-CSF bioactivity. It thus is critically important to define the sub-groups of IBD patients who will benefit from therapeutic modulation of GM-CSF bio-activity.

CD11b as a Biomarker of GM-CSF Bioactivity In Vivo.

CD11b is a cell-surface adhesion molecule present on myeloid cells, the concentration of which increases in response to a wide variety of inflammatory stimuli. GM-CSF priming increases cell-surface levels of CD11b on neutrophils, which promotes their adhesion to vascular endothelium, a critical event in recruitment of neutrophils into infected tissues. GM-CSF autoantibodies block the GM-CSF-stimulated increase in cell surface CD11b levels in PAP patients (Uchida et al, NEJM, 2007). Addition of exogenous GM-CSF to whole blood from a patient can be used to measure the ability to stimulate this change in neutrophil CD11b levels and is the basis of an assay known as the CD11b stimulation index (Uchida et al, NEJM, 2007, incorporated herein by reference).

The present invention provides novel kits and methods for the classification, characterization, and prediction of outcome in patients having inflammatory bowel diseases. The present invention further relates to kits and methods that may be used to determine the prognosis of an individual having an inflammatory bowel disease, or to determine the optimal choice of treatment for such individuals.

Anti-GM-CSF Antibody Concentration and IBD Phenotype

In one aspect of the invention, levels of anti-GM-CSF antibody can be measured and used to classify individuals having an inflammatory bowel disease. It has been found that IBD patients exhibit a range of anti-GM-CSF antibody levels, with patients with small bowel CD ($CD_{SB}$) exhibiting high levels, and patients with UC exhibiting low levels, relative to patients with colonic CD and healthy controls. The elevated anti-GM-CSF levels in patients with $CD_{SB}$ are in the range which inhibits neutrophil function. Serum levels of anti-GM-CSF independently regulate neutrophil function and IBD phenotype, relative to CARD15 genotype and current IBD serological markers. Comparing patients with ileal or ileo-colonic disease grouped together as small bowel CD ($CD_{SB}$), and patients with colonic CD grouped as $CD_C$, we have found for the first time that $CD_{SB}$ patients have increased circulating levels of anti-GM-CSF antibodies, while UC patients have decreased levels of anti-GM-CSF antibodies, relative to $CD_C$ or healthy controls.

Figure 1:
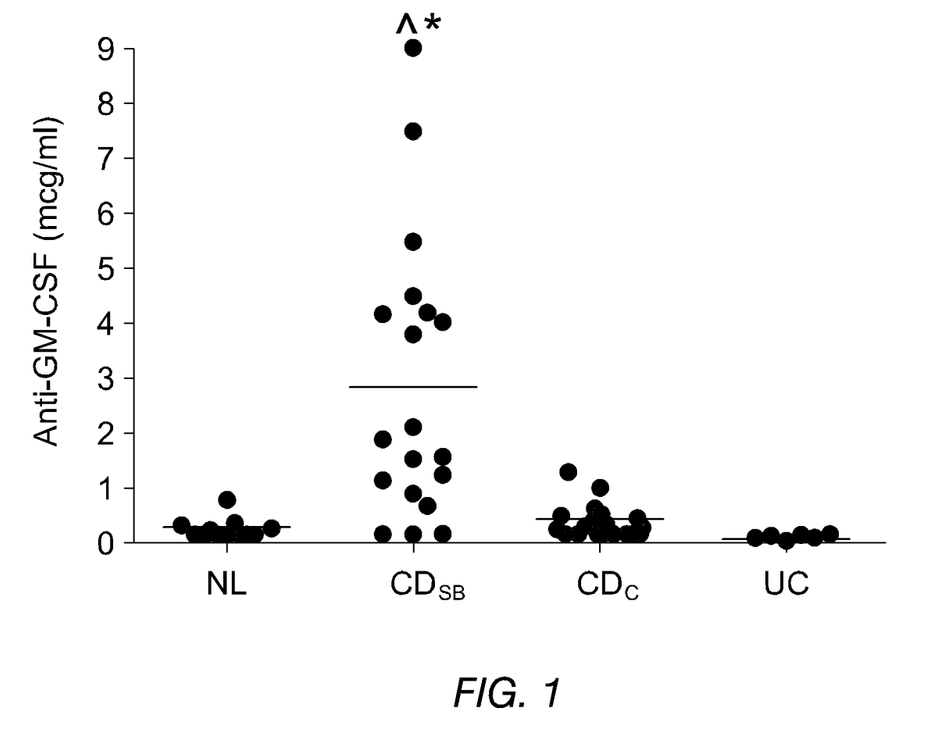
FIG. 1. Anti-GM-CSF Antibody Concentration and IBD Phenotype.

FIG. 1 depicts the relative anti-GM-CSF antibody concentrations in the various IBD subgroups compared to healthy control patients. Serum anti-GM-CSF antibody concentrations were determined by ELISA in IBD sub-groups and healthy controls (NL). FIG. 1 depicts anti-GM-CSF antibody concentration in patients with small bowel Crohn's disease ($CD_{SB}$), patients with Colonic Crohns disease ($CD_C$), and Ulcerative Colitis (UC). The differences between groups were compared by Kruskal-Wallis with post hoc Bonferroni multiple comparisons test. p<0.0001 vs. NL & UC; *p=0.006 vs. $CD_C$. The mean value was as indicated for each group.

It was therefore surprisingly discovered that inflammatory bowel disease patients having small bowel Crohn's disease ($CD_{SB}$) had statistically significant increases in anti-GM-CSF antibody concentration as compared to individuals with colonic Crohn's disease, individuals with ulcerative colitis, and normal individuals. As such, determination of anti-GM-CSF antibody concentration can be used to distinguish subclasses of patients diagnosed with Crohn's disease, providing improved selection of therapeutic treatments and prediction of disease behavior and progression.

In fact, mean (+-SE) serum anti-GM-CSF concentration in ileal $CD_{SB}$ and ileo-colonic $CD_{SB}$ individuals was equal to 2.2 (n=20, and 86, respectively), versus 0.7 mcg/ml (n=51) in CD.sub.C, 0.7 mcg/ml (n=43) in UC, and 0.4 mcg/ml (n=20) in healthy controls. See Table 1.

Thus, in one aspect of the present invention, a method of classifying individuals having an inflammatory bowel disease is provided comprising the steps of obtaining a sample from the individual, determining the concentration of serum anti-GM-CSF concentration in the sample, a mean (+-SE) serum anti-GM-CSF concentration of greater than or equal to about 1 mcg/ml, or greater than or equal to about 1.5 mcg/ml, or greater than or equal to about 2.0 mcg/ml, or within the range of about 1.0 mcg/ml to 2.5 mcg/ml, indicates that the individual is likely to have ileal or ileo-colonic Crohn's disease.

Importantly, anti-GM-CSF levels did not change in CD patients who had achieved clinical remission with anti-TNF therapy (2.4.+-0.0.8 mcg/ml vs 3.3.+-0.1.3 mcg/ml, n=6), indicating that these are a stable feature of their disease, and do not simply reflect a response to mucosal inflammation.

The instant invention further relates to a method of modulating IBD phenotype or treating individuals having an IBD using exogenously or endogenously administered GM-CSF.

Figure 2A:
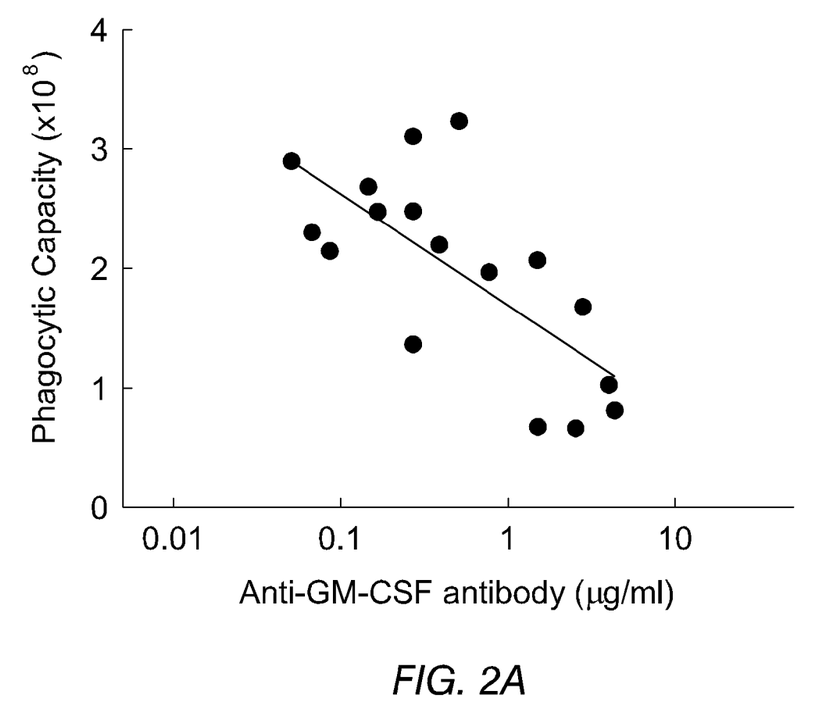
FIGS. 2A and 2B. Function of anti GM-CSF antibodies and Neutrophil Phagocytosis in Healthy Individuals and Individuals with Inflammatory Bowel Disease and PAP.
Figure 2B:
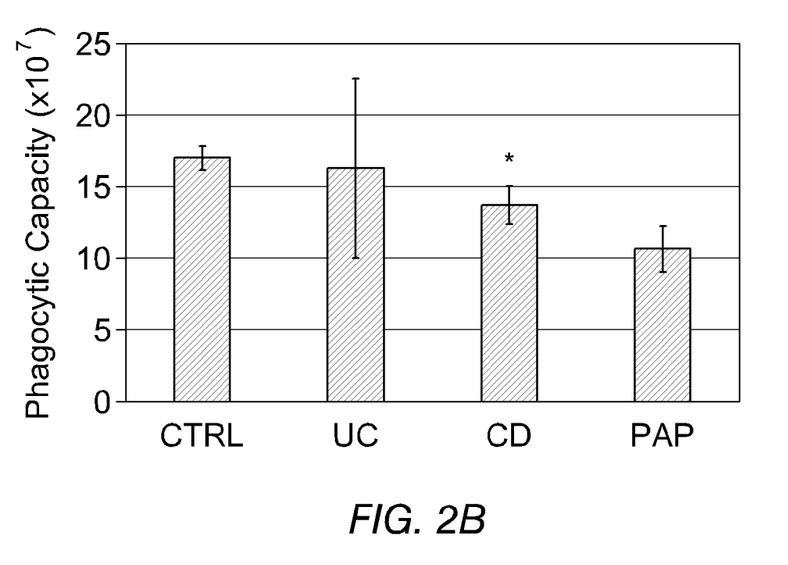

As shown in FIGS. 2A and B, anti-GM-CSF antibodies in the range observed in $CD_{SB}$ can regulate (i.e., neutralize) GM-CSF bioactivity and neutrophil function, thereby creating a functional GM-CSF deficiency in the individual.

We assessed the potential significance of this finding by quantifying neutrophil phagocytosis with a sensitive assay. FIGS. 2A and B depict the results of this study. FIG. 2a depicts neutrophil phagocytosis measured in whole blood. Each dot represents four determinations per individual. αGM-CSF-antibody levels were done in triplicate for each individual. Results demonstrated that neutrophil phagocytic capacity correlated inversely with αGM-CSF antibody levels, over the range observed in IBD patients (n=17; R.sup.2=0.51; FIG. 2a). We have found that neutrophil phagocytosis in whole blood is significantly reduced in Crohn's Disease patients, relative to healthy controls (see FIG. 2b). This reduction was intermediate between healthy controls and that observed in PAP patients, and suggests that the elevated anti-GM-CSF antibodies observed in the Crohn's Disease patients do have a significant effect upon neutrophil phagocytosis.

Figure 3:
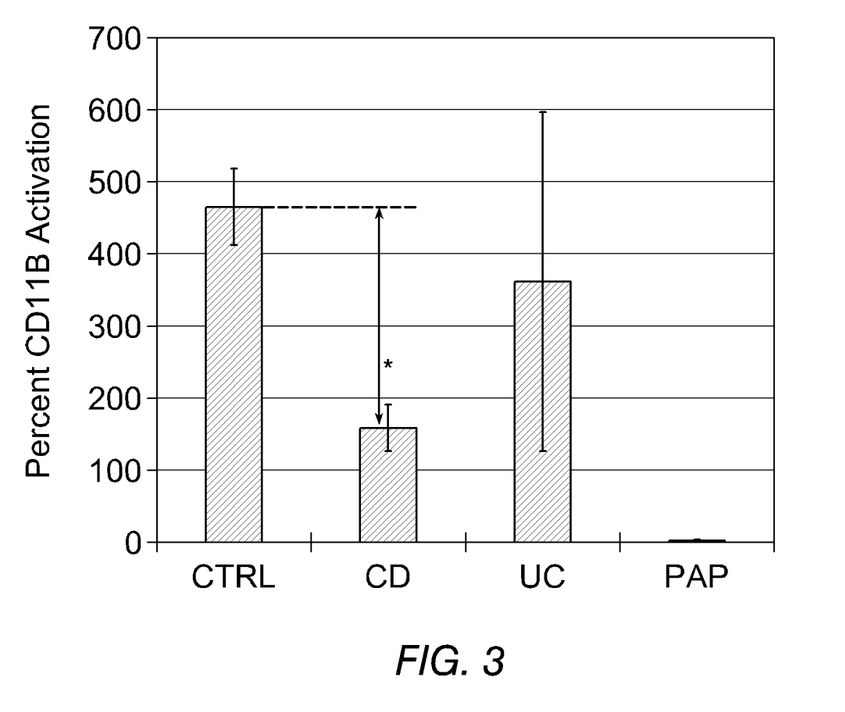
FIG. 3. CM-CSF activation of CD11b in Inflammatory Bowel Disease

We then asked whether GM-CSF bioactivity, as measured by CD11b activation on neutrophils in whole blood, would also be reduced in Crohn's Disease patients. As shown in FIG. 3, we have found that GM-CSF dependent CD11b activation on neutrophils is significantly reduced in Crohn's Disease patients, relative to healthy controls.

Taken together, these studies have identified anti-GM-CSF as a novel regulator of neutrophil function and IBD phenotype. Further these studies establish the predictive value of the serum anti-GM-CSF antibody with regard to IBD phenotype. The risk associated with the serum anti-GM-CSF antibody level with regard to IBD phenotype and behavior is at least comparable to that associated with CARD15 SNP carriage, suggesting a functional interaction. More importantly, as both GM-CSF administration and GM-CSF neutralization are in development as therapies for inflammatory bowel diseases and other autoimmune disorders, this raises the possibility that determination of the anti-GM-CSF level in an individual patient may guide biologic therapy, in terms of whether augmentation or inhibition of GM-CSF bioactivity would be beneficial.

CD11b activity in response to exogenous GM-CSF may be used as a biomarker to classify subtypes of inflammatory bowel disease, wherein individuals having reduced CD11b activity are more likely to have CD, and less likely to have UC. Thus, in this aspect of the present invention, determination of CD11b activity, particularly in response to GM-CSF, may be used as a diagnostic assay to classify subtypes of inflammatory bowel disease, particularly ulcerative colitis and Crohn's disease. In one aspect, CD11b activity on monocytes is measured to distinguish between CD and UC patients. In another aspect, CD11b activity on neutrophils is determined to distinguish between CD and UC patients. Such classification of IBD patients permits targeted therapy and prediction of disease characteristics, behavior and likely outcome.

In yet another aspect, the instant invention provides a method of performing an overall risk assessment, comprising the steps of obtaining a serum sample from a individual suspected of having an IBD, determining the concentration of anti-GM-CSF relative to neutrophil function, IBD phenotype, CARD15 variants or commercial IBD serology to obtain a ratio, then using the determined ratio to determine whether the individual has Crohn's disease or whether an individual having an IBD has a high likelihood of disease progression and surgery. The commercial IBD serology includes, for example, ASCA, pANCA, CBir1, I2, or OmpC antibodies. The disclosure of U.S. Pat. No. 6,218,129 Walsh et al., U.S. Pat. No. 6,183,951, Plevy et al., and U.S. Pat. No. 5,932,429 Targan et al., describing methods of diagnosing IBD are all incorporated herein by reference.

In another aspect of the instant invention, the novel biomarkers and methods disclosed herein may be used to predict or determine inflammatory bowel disease location and behavior via measurement or detection of anti-GM-CSF antibody concentrations with or without the presence of the CARD15 single nucleotide polymorphism.

Table 1 depicts data representing the interactions between the CARD15 Crohn's Disease (CD) susceptibility gene and anti-GM-CSF antibody with respect to disease location and behavior. In Table 1, the demographic characteristics and CD location for a cohort of pediatric onset IBD patients are shown, together with the frequency of CARD15 SNP carriage, stricturing or penetrating behavior (B2/B3), and surgery. Serum anti-GM-CSF (mcg/ml) is given as the median (25th, 75th percentile), a, b, c, d, e=p<0.05 by Kruskal-Wallis test with Dunn's multiple comparison test versus the indicated group. The patients have been followed for a median (25th, 75th percentile) of 4 (2, 6) years from diagnosis. The diagnosis of CD or UC is made based upon established endoscopic, histological, and radiographic criteria (Hanauer S. B. 2006). In this system, ileal involvement is classified as L1, colonic as L2, and ileo-colonic as L3. CD phenotype is assigned as per the Montreal classification, with patients with ileal or ileo-colonic disease grouped together as small bowel CD (CD.sub.SB), and patients with colonic CD grouped as CD.sub.0 (Satsangi J. 2006).

The individuals have been genotyped for the three predominant CARD15 CD susceptibility SNPs (R702w, G908R and 1007fs). Carriage of at least one SNP has been recorded as positive with respect to the current analysis. Serum anti-GM-CSF concentrations may be determined using an ELISA as described in the Examples herein. Genotyping for the NOD2/CARD15 variants associated with CD, R702W (SNP8), G908R (SNP12), and 1007fs (SNP13) is performed using the protocol published in Tomer G. 2003, incorporated herein by reference. Titers of the ASCA, OmpC, I2, and CBir1 antibodies which are associated with small bowel CD, and pANCA, which is associated with UC and colonic CD, may be determined by a commercial laboratory (Prometheus Laboratories, San Diego, Calif.).

In our studies, 40% to 45% of the CD individuals with ileal or ileocolonic disease exhibited CARD15 SNP carriage and stricturing or penetrating disease behavior over time (B2/B3), with 30% requiring at least one surgery. Consistent with our prior results, we have confirmed that serum anti-GM-CSF is up regulated in CD patients with ileal or ileo-colonic involvement, relative to patients with Crohn's colitis, UC, or healthy controls.

TABLE 1

Anti-GM-CSF and Disease Location and Behavior

| Location | n | Age | Male | CARD15 SNP | Anti-GM-CSF (mcg/ml) | B2/B3 | Surgery |
|---|---|---|---|---|---|---|---|
| L1: Ileal, a | 20 | 13 | 75% | 45% | 2.2 (0.9, 6.7) d, e | 45% | 30% |
| L3: Ileo-colonic, b | 86 | 12 | 52% | 47% | 2.2 (0.7, 9.4) c, d, e | 37% | 33% |
| L2: Colonic, c | 51 | 11 | 61% | 16% | 0.7 (0.4, 1.6) b | 14% | 16% |
| UC, d | 43 | 12 | 60% | 16% | 0.7 (0.2, 1.3) a, b | N/A | 16% |
| Control, e | 20 | 13 | 70% | Not done | 0.4 (0.2, 0.6) a, b | N/A | N/A |

Referring to Table 1, the mean (95% CI) anti-GM-CSF level was equal to 10 (4, 16) mcg/ml in CD patients carrying at least one CARD15 SNP compared to 9 (3, 15) mcg/ml in those without a CARD15 SNP. Similarly, 47% of patients with elevated anti-GM-CSF (≥2 mcg/ml) carried a CARD15 SNP, while 53% did not. This suggested that increased anti-GM-CSF was not simply a function of CARD15 SNP carriage.

The relative risk (RR) for ileal or ileo-colonic involvement ($CD_{SB}$) in a CD patient carrying a CARD15 susceptibility SNP was equal to 5.2, while the RR for a CD patient with an anti-GM-CSF level .gtoreq.2 mcg/ml was equal to 4, and the RR for a CD patient with both an anti-GM-CSF level≥2 mcg/ml and CARD15 SNP was equal to 10.2 (p<0.001 for each). Therefore, elevated anti-GM-CSF levels appear to interact with CARD15 SNPs to increase susceptibility for CD.sub.SB. Importantly, anti-GM-CSF levels did not change over one year in patients who had achieved clinical remission with anti-TNF therapy (2.4+-0.8 mcg/ml vs 3.3+-1.3 mcg/ml, n=6), indicating that these are a stable feature of their disease, and do not simply reflect a response to mucosal inflammation.

The chi-square test of independence has found a significantly different prevalence of L1/L3 (vs. L2), CARD15 mutation, and high anti-GM-CSF (≥2 mcg/ml) in patients with CD compared to patients with UC (p-values<0.0001, 0.0155, 0.0032 respectively). Hence, we have investigated the association of anti-GM-CSF with the disease location, behavior and surgery while controlling for CARD15 mutation, separately in patients with CD and in patients with UC, the results of which are shown in Table 1. The median anti-GM-CSF level was increased two-fold in CD patients with penetrating or stricturing behavior (B2/B3), compared to those with inflammatory behavior (B1). After stratifying for individuals with ileal or ileo-colonic CD, the median anti-GM-CSF level was equal to 1.8 (0.7, 7.7) in those who did not require surgery, versus 6.6 (0.7, 10) in those who did require surgery (p=0.04). Consistent with this, the odds ratio (OR) for surgery in CD patients with elevated anti-GM-CSF was equal to 3.2 (p<0.01).

Using the Cochran-Mantel-Haenszel (CMH) test controlling for CARD15 SNP carriage, it was found that anti-GM-CSF level (high vs. low) is significantly associated with the disease location distribution (L2 vs. L1/L3), the disease behavior distribution (B1 vs. B2/B3) and surgery status (p-values=0.0005, 0.0076, 0.0038 respectively). More specifically, for a CD patient with a high anti-GM-CSF level (≤2 mcg/ml), the disease is less likely to be only colonic (L2) (Relative Risk=0 with CARD15 mutation, 0.63 with no CARD15 mutation), less likely to be non-stricturing, non-penetrating B1 (Relative Risk=0.7366), and more likely treated with a surgery (Relative Risk=2.155), independent of the presence/absence of CARD15 mutation. The mean elapsed time since diagnosis is not significantly different in the patients with high anti-GM-CSF level than in the patients with a low anti-GM-CSF level. Therefore, these results indicate a significant effect of anti-GM-CSF level, independent of CARD15 mutation effect.

In contrast, using the CMH test anti-GM-CSF level (high vs. low) controlling for CARD15 SNP status, is not significantly associated with the surgery status in patients with UC.

As such, one aspect of the present invention provides kits and methods of classifying IBD patients by determining the concentration of anti-GM-CSF antibody in blood or serum samples from individuals suspected of having or diagnosed with IBD. In particular, anti-GM-CSF levels may be used to distinguish CD patients with ileal or ileo-colonic disease (in which surgery is a more likely outcome) from colonic CD patients, UC patients, and normal (healthy) patients. By classifying the IBD patient into a particular subgroup, the appropriate course of therapy may be determined, reducing the likelihood of administering treatments that will not be successful, thereby stemming disease progression and improving the individual's overall quality of life.

For example, determination of anti-GM-CSF antibody levels in an individual also be used to guide biologic therapy, in terms of whether augmentation or inhibition of GM-CSF bioactivity would be beneficial, comprising the steps of obtaining a sample from the individual, determining the concentration of serum anti-GM-CSF antibody concentration in the sample, wherein a mean serum anti-GM-CSF antibody concentration of greater than or equal to about 1 mcg/ml, or great than or equal to about 1.5 mcg/ml, or greater than or equal to about 2.0 mcg/ml, or within the range of about 1.0 mcg/ml to 2.5 mcg/ml indicates an increased risk for disease progression and surgery. In patients having elevated risk of surgery, treatments such as anti-TNF alpha (such as Humira or Remicade), or GM-CSF therapy would be indicated as the preferred therapy. In this regard, the instant methods, and kits embodying these methods, allow for improved treatment of individuals likely to require surgery.

Thus, the present invention is directed to a highly sensitive method of diagnosing, classifying, or characterizing disease in individuals having an inflammatory bowel disease, such that disease progression and/or the appropriate course of treatment may be readily determined, and kits utilizing this method.

A variety of assay formats can be used to determine anti-GM-CSF antibody levels in a sample.

Flow cytometry can be used to determine anti-GM-CSF antibody levels according to a method of the invention. Such flow cytometric assays, including bead based immunoassays, can be used to determine anti-GM-CSF antibody levels in the same manner as used to detect serum antibodies to *Candida albicans* and serum antibodies to HIV proteins (see, for example, Bishop and Davis, J. Immunol. Methods 210:79-87 (1997); McHugh et al., J. Immunol. Methods 116:213 (1989); Scillian et al., Blood 73:2041 (1989), each of which is incorporated by reference herein).

Phage display technology for expressing a recombinant antigen specific for anti-GM-CSF antibodies also can be used to determine the level of anti-GM-CSF antibody. Phage particles expressing the antigen specific for anti-GM-CSF antibody, or an antigen specific for anti-GM-CSF antibody, can be anchored, if desired, to a multiwell plate using an antibody such as an antiphage monoclonal antibody (Felici et al., "Phage-Displayed Peptides as Tools for Characterization of Human Sera" in Abelson (Ed.), Methods in Enzymol. 267, San Diego: Academic Press, Inc. (1996), which is incorporated by reference herein).

A variety of immunoassay formats including competitive and non-competitive immunoassay formats also are useful the methods of the invention (Self and Cook, Curr. Opin. Biotechnol. 7:60-65 (1996), which is incorporated by reference). Immunoassays encompass capillary electrophoresis based immunoassays (CEIA) and can be automated, if desired. Immunoassays also can be used in conjunction with laser induced fluorescence (see, for example, Schmalzing and Nashabeh, Electrophoresis 18:2184-93 (1997)); Bao, J. Chromatogr. B. Biomed. Sci. 699:463-80 (1997), each of which is incorporated herein by reference). Liposome immunoassays, such as flow-injection liposome immunoassays and liposome immunosensors, also can be used to determine anti-GM-CSF antibody concentration.

Immunoassays, such as enzyme-linked immunosorbent assays (ELISAs), can be particularly useful in a method of the invention. An ELISA, for example, can be useful for determining whether a sample is positive for anti-GM-CSF antibodies or for determining the anti-GM-CSF antibody level in a sample. An enzyme such as horseradish peroxidase (HRP), alkaline phosphatase (AP), .beta.-galactosidase or urease can be linked to a secondary antibody selective for anti-GM-CSF antibody, or to a secondary antibody selective for anti-GM-CSF antibody for use in a method of the invention. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a .beta.-galactosidase detection system can be used with the chromogenic substrate o-nitrophenyl-.beta.-D-galactopyranoside (ONPG), which yields a soluble product detectable at 410 nm, or a urease detection system can be used with a substrate such as urea-bromocresol purple (Sigma Immunochemicals, St. Louis, Mo.). A useful secondary antibody linked to an enzyme can be obtained from a number of commercial sources; goat F(ab').sub.2 anti-human IgG-alkaline phosphatase, for example, can be purchased from Jackson Immuno-Research (West Grove, Pa.).

A radioimmunoassay also can be useful for determining the level of anti-GM-CSF antibodies in a sample. A radioimmunoassay using, for example, an iodine$^{125}$ labeled secondary antibody (Harlow and Lane, Antibodies A Laboratory Manual Cold Spring Harbor Laboratory: New York, 1988, which is incorporated herein by reference) is encompassed within the invention.

A secondary antibody labeled with a chemiluminescent marker also can be useful in the methods of the invention. Such a chemiluminescent secondary antibody is convenient for sensitive, non-radioactive detection of anti-GM-CSF antibodies and can be obtained commercially from various sources such as Amersham Lifesciences, Inc. (Arlington Heights, Ill.).

In addition, a detectable reagent labeled with a fluorochrome can be useful in the methods of the invention for determining the levels of anti-GM-CSF antibody in a sample. Appropriate fluorochromes include, for example, DAPI, fluorescein, Hoechst. 33258, R-phycocyanin, B-phycoerythrin, R-phycoerythrin, rhodamine, Texas red or lissamine. A particularly useful fluorochrome is fluorescein or rhodamine. Secondary antibodies linked to fluorochromes can be obtained commercially. For example, goat F(ab')$_2$ anti-human IgG-FITC is available from Tago Immunologicals (Burlingame, Calif.).

A signal from the detectable reagent can be analyzed, for example, using a spectrophotometer to detect color from a chromogenic substrate; a radiation counter to detect radiation, such as a gamma counter for detection of iodine-125; or a fluorometer to detect fluorescence in the presence of light of a certain wavelength. For detection of enzyme-linked reagents, a quantitative analysis of the amount of anti-GM-CSF antibody can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

Immunoassays using a secondary antibody selective for anti-GM-CSF antibodies are particularly useful in the methods of the invention. As used herein, the term "antibody" means a population of immunoglobulin molecules, which can be polyclonal or monoclonal and of any isotype. As used herein, the term "antibody" encompasses an immunologically active fragment of an immunoglobulin molecule. Such an immunologically active fragment contains the heavy and light chain variable regions, which make up the portion of the antibody molecule that specifically binds an antigen. For example, an immunologically active fragment of an immunoglobulin molecule known in the art as Fab, Fab' or F(ab')$_2$ is included within the meaning of the term antibody.

Using the above-described methods, an individual may be identified as being an optimal candidate for GM-CSF treatment. "GM-CSF" refers to a protein that stimulates the production of granulocytes and macrophages by stem cells. GM-CSF used in the practice of the invention includes any pharmaceutically safe and effective human GM-CSF (e.g., the human GM-CSF with amino acid having the following sequence: Ala Pro Ala Arg Ser Pro Ser Pro Ser Thr Gln Pro Trp Glu His Val Asn Ala Ile Gln Glu Ala Arg Arg Leu Leu Asn Leu Ser Arg Asp Thr Ala Ala Glu Met Asn Glu Thr Val Glu Val Ile Ser Glu Met Phe Asp Leu Gln Glu Pro Thr Cys Leu Gln Thr Arg Leu Glu Leu Tyr Lys Gln Gly Leu Arg Gly Ser Leu Thr Lys Leu Lys Gly Pro Leu Thr Met Met Ala Ser His Tyr Lys Gln His Cys Pro Pro Thr Pro Glu Thr Ser Cys Ala Thr Gln Ile Ile Thr Phe Glu Ser Phe Lys Glu Asn Leu Lys Asp Phe Leu Leu Val Ile Pro Phe Asp Cys Trp Glu Pro Val Gln Glu (SEQ ID NO:1)), or any derivative thereof having the biological activity of human GM-CSF. Derivatives of GM-CSF may be (i) one in which one or more of the amino acid residues of the protein are substituted with a conserved or non-conserved amino acid residue, and such substituted amino acid residue may or may not be one encoded by the genetic code, (ii) one in which one or more of the amino acid residues of the protein include a substituent group, (iii) one in which the mature protein is fused with another compound, such as a compound to increase the half-life or the polypeptide (for example, polyethyleneglycol), (iv) one in which additional amino acids are fused to the mature protein, such as a leader or secretory sequence or a sequence which is employed for purification of the mature protein, or (v) one in which the protein is fused with a larger protein, i.e., an antibody or Fc. Examples of GM-CSFs include, but are not limited to, native GM-CSF, molgramostim (bacteria-derived GM-CSF), ragramostim (CHO-derived GM-CSF), sargramostim (Leukine—yeast-derived GM-CSF), and pegylated GMCSF (i.e., pegylated native GM-CSF or pegylated GMCSF derived from any source).

Recombinant GM-CSF may be used with the methods of the instant invention. "Recombinant GM-CSF" refers to either to GM-CSF synthesized in a cell into which a nucleic acid encoding exogenous GM-CSF has been introduced, or a cell in which the endogenous GM-CSF gene has been stimulated to overproduce GM-CSF by the introduction of regulatory elements that induce a high rate of transcription of the endogenous GM-CSF gene.

The GM-CSF used may be recombinant human GM-CSF (rhu GM-CSF), such as Leukine®. (Berlex Inc., Bothell, Wash.). Leukine® (generically termed "sargramostim") is a biosynthetic, yeast-derived, recombinant human GM-CSF, consisting of a single 127 amino acid glycoprotein that differs from the endogenous human GM-CSF shown having the sequence as set forth above in which arginine is substituted with leucine at position 23. Leukine® is produced in the yeast *Saccharomyces cerevisiae*.

Leukine® has been shown to exhibit the same hematopoietic effects as those induced by endogenous GM-CSF, namely, the stimulation of progenitor cells committed along the granulocyte-macrophage pathway to form neutrophils, monocytes, macrophages, and eosinophils (Technical Product Report: Leukine® Liquid, Immunex Corporation, Seattle, Wash., 1997, which is herein incorporated by reference). Leukine®, like endogenous GM-CSF, also promotes the differentiation of progenitor cells giving rise to erythrocytes and megakaryocytes. In addition to stimulating hematopoiesis, Leukine® enhances many of the functional activities of mature neutrophils, monocytes and macrophages, such as chemotaxis, growth factor secretion, anti-tumor activity, antibacterial and antifungal activities, and so on.

Leukine® Liquid is a sterile injectable aqueous solution generally sold in 1 ml vials containing 500 .mu.g/ml (2.8.times.10.sup.6 IU) sargramostim; 40 mg/ml mannitol; 10 mg/ml sucrose; 1.2 mg/ml tromethamine; sterile water; and 1.15% benzyl alcohol. LEUKINE® Lyohphilized is also sold, and typically is packaged in vials containing a sterile lyophilized powder for reconstitution with 1 ml sterile water. LEUKINE® Lyophilized may contain 250 µg or 500 µg sargramostim (1.4 or 2.8.times.10$^6$ IU); 40 mg mannitol; 10 mg sucrose; and 1.2 mg tromethamine. LEUKINE® Liquid and reconstituted solutions of LEUKINE® Lyophilized are stored refrigerated at 2-8.degree. C.

Typically, the aqueous solution of GM-CSF is administered by subcutaneous injection or intravenous infusion. However, other methods such as oral, intraperitoneal, subdermal, and intramuscular administrations may be used. Doses delivered may be the same as those delivered to stimulate an immune response in humans for other disease purposes. In certain embodiments, doses may be about 100 to about 1500 µg (including any values therebetween, such as about 250, 500, and 1000 µg) once per week when administered via subcutaneous injection.

The methods of administration of GM-CSF as described in US 2007/0041938, Pettit, et al. are incorporated herein by reference.

In addition, using the above-described methods, patients may be identified that would benefit from administration of anti-TNF. This therapy is sold under the trade name Humira®, and is described in U.S. Pat. No. 6,090,382, Salfeld et al., incorporated herein by reference. This therapy is administered using standard methods as known to one of ordinary skill in the art.

The following examples are intended to illustrate but not limit the present invention.

EXAMPLE I

Determining Anti-GM-CSF Antibody Activity for Classification of Subtypes

GM-CSF concentration in whole blood or serum samples obtained from a patient suspected of having an inflammatory bowel disease is determined using the methods as described in Uchida, et al. Blood, 2004, incorporated herein by reference, and described herein.

Anti-GM-CSF antibodies are assayed using serum samples that are either immediately obtained or previously collected and stored at −70° C. until analysis. Anti-GM-CSF antibody concentration of a serum sample from an individual of interest is then measured. The serum sample is diluted 1:100, 1:1000 and 1:3000 with phosphate buffered saline (PBS) containing 1% bovine serum albumin and 0.1% Tween 20. Separate 50 μl aliquots of diluted serum and the affinity-purified anti-GM-CSF antibody isolated from the serum of patients with pulmonary alveolar proteinosis as a standard (0-50 ng/ml) were incubated at room temperature for 40 minutes in ELISA plates previously coated overnight at 4° C. with 1 μg/ml rhGM-CSF (Leukine® Berlex) and blocked for 1 hour with StabilCoat® (SurModics). After washing five times with PBS 0.1% Tween 20 (PBST), anti-GM-CSF antibody captured by rhGM-CSF is detected by peroxidase labeled anti-human IgG $F(ab)_2$ antibody (Sigma). Tetramethylbenzidine is used as a substrate and absorbance is measured at 450 nm after stopping the reaction with 1N sulfuric acid. Assays are performed in duplicate and the mean of the two results used.

EXAMPLE II

Anti-GM-CSF Concentration as a Predictor of Disease Behavior

The methods of Example 1 are carried out essentially as described above. Following performance of the above-described methods, the values obtained from the assay are then used to classify the individual as either having colonic, or ileal or ileo-colonic. Values greater than or equal to about 2 mcg/ml indicate that the disease behavior is less likely to be only colonic (L2), less likely to be non-stricturing, non-penetrating (B1), and more likely to be treated with a surgery. Assessment of the presence or absence of the CARD15 mutation is not necessary for this determination.

EXAMPLE III

Determining CD11b Stimulation Index for Classification of Subtypes

The CD11b Stimulation Index on neutrophils from whole blood samples obtained from an individual suspected of having an inflammatory bowel disease is determined using the methods as described in Uchida, et al. NEJM, 2007, incorporated herein by reference, and described herein. Briefly, this assay is performed using whole blood samples from IBD patients or healthy controls in the absence or presence of stimulation with exogenously added GM-CSF and then cell surface CD11b is quantified on neutrophils (and/or also on monocytes and eosinophils) is then measured by flow cytometry. Neutrophils can be identified with the high expression level of CD16 determined by fluorescein isothiocyanate (FITC)-conjugated anti-CD16 antibody. Monocytes can be determined APC-conjugated anti-CD 14 antibody. Eosinophils can be determined moderate expression of CD16 and specific cell size and complexity. This assay provides a method to quantify the level of neutrophil (as well as monocyte and eosinophil) innate immune function in IBD patients.

The phycoerythrin (PE)-conjugated monoclonal antibodies against CD11b is purchased from BD Biosciences (San Jose, Calif., USA). CD11b modulates the adherence of polymorphonuclear neutrophils and monocytes to fibrinogen and positive ICAM-1 endothelia.

Preparation for Flow-Cytometry Analyses

Heparinized whole blood is incubated for 30 minutes in the presence or absence of 10 ng of human GM-CSF per milliliter (Leukine, Berlex) or 10 ng of mouse GM-CSF per milliliter (R&D Systems) and incubated for 30 minutes. The samples (50 μL) are then mixed with 50 μL PBS in polystyrene round-bottom tubes (5 mL Falcon, BD-Pharmingen, Heidelberg, Germany) and incubated with incubated with 5 μl, undiluted FITC-, APC- and PE-conjugated antibodies for 30 minutes on ice in the dark. The reaction is stopped and cells are fixed by washing the suspension with 3 ml of BD FACS Lysing solution (BD Biosciences).

Flow cytometry is performed with a FACS Calibur flow cytometer (BD Biosciences) equipped with a 15-mW argon laser emitting at 488 nm. The fluorescence signals of FITC and PE are detected with 530/30 nm (channel 1) and 585/42 nm band pass filters (channel 2) with correction of the spectral overlap by color compensation. Calibration of the flow cytometer is performed using standard fluorescent microbeads (CaliBRITE, BD Biosciences). Analysis of the fluorescence properties of 50,000 events is performed using CellQuest software (BD Biosciences). The increase in CD11b levels after GM-CSF priming (CD11b stimulation index) is calculated as the mean fluorescence intensity of CD11b primed by GM-CSF minus that of CD11b on nonprimed samples, divided by the mean fluorescence intensity of nonprimed samples and multiplied by 100.

GM-CSF stimulation of CD11b on neutrophils (and/or monocytes or eosinophils) is (are) compared to the corresponding cell types in a control group (such as normal, healthy controls) or known standards such as patients diagnosed with small bowel Crohn's disease or ulcerative colitis. A determination that reduced or absent GM-CSF-mediated increase in cell surface CD11b levels in a sample is one mechanism to confirm that the increased level of GM-CSF autoantibodies have functional significance with respect to GM-CSF bioactivity in a given IBD patient.

The foregoing description of examples and embodiments of the subject application has been presented for purposes of illustration and description. It is not intended to be exhaustive or to limit the subject application to the precise form disclosed. Obvious modifications or variations are possible in light of the above teachings. The embodiments were chosen and described to provide the best illustration of the principles of the subject application and its practical application to thereby enable one of ordinary skill in the art to use the subject application in various embodiments and with various modifications as suited to the particular use contemplated. All such modifications and variations are within the scope of the subject application as determined by the appended claims when interpreted in accordance with the breadth to which they are fairly, legally and equitably entitled.

The invention claimed is:

1. A method for the diagnosis and treatment of an inflammatory bowel disease in a subject comprising:
    (a) measuring the concentration of anti-GM-CSF antibodies in a serum sample obtained from the subject;
    (b) diagnosing whether the subject has an inflammatory bowel disease, or the severity of an inflammatory bowel disease, based upon an increased concentration of the anti-GM-CSF antibodies in the sample as compared to the concentration of anti-GM-CSF antibodies in serum from a subject not having an inflammatory bowel disease; and
    (c) administering a therapy to the diagnosed subject, wherein the therapy is selected from the group consisting of an effective amount of anti-TNFα antibodies, an effective amount of GM-CSF, and surgery.

2. The method according to claim 1, wherein the inflammatory bowel disease is selected from the group consisting of small bowel Crohn's disease ($CD_{SB}$), Colonic Crohn's disease ($CD_C$), and Ulcerative Colitis (UC).

3. The method according to claim 1, wherein the increased concentration of anti-GM-CSF antibodies is indicative of the severity of the inflammatory bowel disease.

4. The method of claim 1, wherein the concentration of anti-GM-CSF antibodies in the sample is indicative of a stricturing or penetrating disease state.

5. The method of claim 1, wherein the therapy is an effective amount of anti-TNFα antibodies.

6. The method according to claim 1, further comprising detecting the level of GM-CSF dependent up-regulation of cell surface CD11b in the sample.

7. The method according to claim 1, wherein (a) further comprises:
    washing the complex to remove non-specifically bound components; and
    detecting the antigen-antibody complex.

8. The method of claim 1, wherein the GM-CSF comprises sargramostim.

9. A method for the prognosis and treatment of an inflammatory bowel disease in a patient comprising:
    (a) determining the concentration of anti-GM-CSF antibodies in a serum sample obtained from the patient comprising contacting the sample with an immobilized GM-CSF; and
    (b) determining whether the patient has an increased risk of the inflammatory bowel disease progressing based upon increased binding of the GM-CSF to the anti-GM-CSF antibodies as compared to the binding of GM-CSF to anti-GM-CSF antibodies in a serum sample from a subject not having an inflammatory bowel disease; and
    (c) administering an effective amount of anti-TNFα antibodies to the patient having the increased risk of disease progression.

10. The method of claim 9, wherein the concentration of anti-GM-CSF antibodies in the sample obtained from the patient is greater than or equal to about 1.5 µg/ml is indicative of an increased risk of disease progression.

11. A method for the prognosis and targeted treatment of an inflammatory bowel disease in a patient comprising:
    (a) measuring an increased concentration of anti-GM-CSF antibodies in a serum sample obtained from the patient compared to the concentration of anti-GM-CSF antibodies in a sample from a subject not having an inflammatory bowel disease
    (b) determining whether the patient has an increased risk of inflammatory bowel disease progression when the increased concentration of anti-GM-CSF antibodies is measured; and
    (c) administering an effective amount of anti-TNFα antibodies to the patient having an increased risk of inflammatory bowel disease progression.

12. The method according to claim 11, wherein the inflammatory bowel disease is selected from the group consisting of small bowel Crohn's disease ($CD_{SB}$), Colonic Crohn's disease ($CD_C$), and Ulcerative Colitis (UC).

13. The method of claim 11, wherein the sample obtained from the patient comprises an antibody selected from the group consisting of anti-*saccharomyces cervisiae* antibody, anti-neutrophil cytoplasmic antibody with perinuclear staining, anti-CBir1 antibody, anti-I2 antibody, and anti-OmpC antibody.

14. The method according to claim 11, wherein the concentration of anti GM-CSF antibodies is determined by a method comprising:
    providing an immobilized GM-CSF;
    contacting the sample with the GM-CSF to form an antigen-antibody complex;
    washing the complex to remove non-specifically bound components; and
    detecting the antigen-antibody complex.

15. The method of claim 14, wherein the immobilized GM-CSF is sararamostim.

16. The method of claim 11, wherein the concentration of the anti-GM-CSF antibodies in a serum sample obtained from the patient is greater than 1.5 μg/ml.

17. The method of claim 11, wherein (a) comprises comparing the concentration of anti-GM-CSF antibodies in a serum sample obtained from the patient compared to the concentration of anti-GM-CSF antibodies in a sample from a subject not having an inflammatory bowel disease.

* * * * *

UNITED STATES PATENT AND TRADEMARK OFFICE
CERTIFICATE OF CORRECTION

PATENT NO. : 9,541,560 B2
APPLICATION NO. : 14/686628
DATED : January 10, 2017
INVENTOR(S) : Lee Denson et al.

Page 1 of 1

It is certified that error appears in the above-identified patent and that said Letters Patent is hereby corrected as shown below:

On the Title Page

In Column 2 (page 1, item (56)) at Line 4, Under Other Publications, change "Electroneic" to --Electronic--.

In Column 2 (page 1, item (56)) at Line 17, Under Other Publications, change "$0_2$" to --$O_2$--.

In the Specification

In Column 3 at Line 17, Change "cervisiae" to --cerevisiae--.

In Column 6 at Line 26, After "Disease" insert --.--.

In Column 15 at Line 1, Change "than" to --then--.

In Column 18 at Line 31 (approx.), Change "Lyohphilized" to --Lyophilized--.

In Column 19 at Line 21 (approx.), Change "$F(ab)_z$" to --$F(ab)_2$--.

In the Claims

In Column 23 at Line 7, In Claim 13, change "cervisiae" to --cerevisiae--.

In Column 23 at Line 21, In Claim 13, change "cervisiae" to --cerevisiae--.

Signed and Sealed this
Twenty-fifth Day of April, 2017

Michelle K. Lee
*Director of the United States Patent and Trademark Office*